United States Patent [19]

Fields et al.

[11] 4,427,565

[45] Jan. 24, 1984

[54] NOVEL CLASS OF RUST INHIBITORS FOR FUELS AND OILS

[75] Inventors: Ellis K. Fields, River Forest; Ronald L. Anderson, Naperville, both of Ill.

[73] Assignee: Standard Oil Company (Indiana), Chicago, Ill.

[21] Appl. No.: 480,889

[22] Filed: Mar. 31, 1983

Related U.S. Application Data

[62] Division of Ser. No. 287,156, Jul. 27, 1981, Pat. No. 4,388,470.

[51] Int. Cl.$^3$ .............................................. C10M 1/20
[52] U.S. Cl. .................................... 252/56 D; 44/63; 252/396
[58] Field of Search ................. 44/63; 252/56 D, 396; 549/240

[56] References Cited

U.S. PATENT DOCUMENTS 2,365,703  12/1944  John ................................... 549/240
4,388,470   6/1983  Fields et al. ....................... 549/240

*Primary Examiner*—Jacqueline V. Howard
*Attorney, Agent, or Firm*—Gunar J. Blumberg; William T. McClain; William H. Magidson

[57] ABSTRACT

Novel rust inhibitors for hydrocarbon fuels and oils are provided. Also, novel photo-adducts of dimethylmaleic anhydride and olefins useful as rust inhibitors.

3 Claims, No Drawings

NOVEL CLASS OF RUST INHIBITORS FOR FUELS AND OILS

This is a division, of application Ser. No. 287,156 filed July 27, 1981, now U.S. Pat. No. 4,388,470.

FIELD OF THE INVENTION

The field of this invention relates to a novel class of rust inhibitors for hydrocarbon fuels, such as gasoline and kerosene, and oils and to novel chemical compounds useful as fuel and rust inhibitors.

BACKGROUND

The field of this invention relates to rust inhibitors for fuels and oils, particularly that photo-adducts of dimethylmaleic anhydride with olefins function effectively as rust inhibitors for fuels and oils.

It is an object of this invention to provide photo-adducts of dimethylmaleic anhydride with olefins as rust inhibitors for hydrogen fuels, such as gasoline, kerosene, etc., and oils. Another object is to provide novel compositions of matter. Further objects and advantages will become apparent as the description of the invention proceeds.

We have discovered novel rust inhibitors for liquid hydrocarbon fuels and oils. These rust inhibitors are photo-adducts of dimethylmaleic anhydride with olefins. The prior art has not recognized that photo-adducts of dimethyl maleic anhydride with olefins are useful as rust inhibitors for fuels and oils.

An article by G. O. Schenck, W. Hartman, and R. Steinmetz in Chem. BER. 96, 498 (1963) discloses the preparation of certain olefin photo-adducts with dimethylmaleic anhydride using a high-pressure arc as a source of ultra violet light. However, the prior art never contemplated the use of these compounds as rust inhibitors for fuels and oils; also certain novel compositions of matter are prepared by our novel process.

We have discovered that the photo-adducts of dimethylmaleic anhydride with olefins are effective rust inhibitors for fuels and oils. The olefins have the following structure:

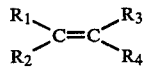

wherein $R_1$ through $R_4$ are the same or different alkyl or aralkyl groups containing 1 to 30 carbon atoms. Alternatively, one R group is an alkyl or aralkyl group and the other three R groups are hydrogen. If desired the R groups are suitably linked, as in cycloalkylolefins.

It is preferred to make the rust inhibitors for fuels and oils utilizing terminal olefins containing 8 to 30 carbon atoms.

Our novel rust inhibitors are effective with any hydrocarbon fuels, such as gasoline or kerosene or oil. Representative oils include automotive oils, railway diesel oils, turbine oils, and cutting oils. Our novel rust inhibitors are particularly effective rust inhibitors in concentrations of about 10 to 10,000 parts per million.

According to our novel process, dimethylmaleic anhydride forms photo-adducts with olefins when irradiated in solution in the presence of a sensitizer such as benzophenone, acetophenone, acetone, Rose Bengal, or methylene blue. The products are derivatives of cyclobutane. The following novel compositions useful as rust inhibitors for hydrocarbon fuels and oils were prepared utilizing our novel process.

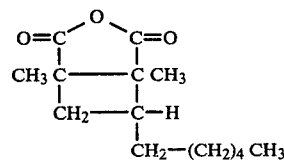

1,2-dimethyl-3-n-hexylcyclobutane-1,2-dicarboxylic anhydride

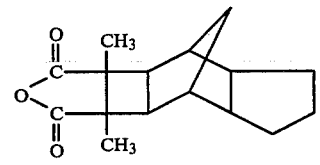

and

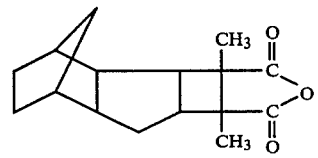

The following examples illustrate the preferred embodiments of this invention. It will be understood that these examples are for illustrative purposes only and do not purport to be wholly definitive with respect to conditions or scope of the invention.

EXAMPLE 1

A solution of 7.56 g (60 mm) of dimethylmaleic anhydride and 1 g of benzophenone in 62.6 ml (0.4 mole) of 1-octene in a 250 ml Pyrex Erlenmeyer flask was irradiated by a G. E. Sunlamp at 25° C. for 15.5 hours. The mixture was filtered to recover 1.8 g unreacted dimethylmaleic anhydride; the filtrate was distilled to a pot temperature of 135° C. at 200 torr. to recover 53 ml of 1-octene. The pot residue, slightly hazy, was filtered through Celite to give 10.5 g of colorless, viscous product that analyzed C,70.9%; H,8.8%. Calculated for $C_{14}H_{22}O_3$: C,70.6%; H,9.2%. Chemical shifts in the $^{13}C$ nmr, assignment, confirmed by off-resonance decoupling, were:

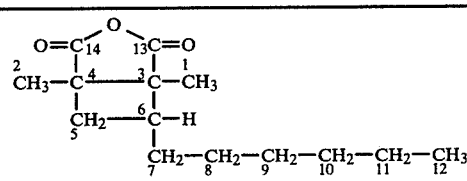

| C atom | $^{13}C$ δ tms | C atom | $^{13}C$ δ tms |
|---|---|---|---|
| 1 | 9.0 | *8 | 26.8 |
| 2 | 16.6 | 9 | 29.0 |
| 3 | 45.8 | 10 | 31.7 |
| 4 | 50.0 | 11 | 22.5 |
| 5 | 36.3 | 12 | 14.6 |
| 6 | 39.3 | *13 | 175.4 |
| *7 | 31.2 | *14 | 176.1 |

*assignments could be reversed.

Selectivity was 100% at 73% conversion.

EXAMPLE 2

A mixture of 7.56 g (60 mm) of dimethylmaleic anhydride, 1 g of benzophenone, 19.15 ml (60 mm) 1-octadecene, and 50 ml of isopropyl ether was refluxed over a G. E. Sunlamp for 64 hours. The mixture was cooled to 20° C., filtered from 1.1 g of dimethylmaleic anhydride photo-dimer, and evaporated, giving a white solid, 21.1 g (93%), that melted at 66°–68° C. after 1 crystallization from n-hexane. Analysis: Calcd. for $C_{24}H_{42}O_3$: C,76.2%; H,11.1%. Found: C,76.3%; H,11.2%. The $^{13}C$ nmr, assignments confirmed by off-resonance decoupling, were:

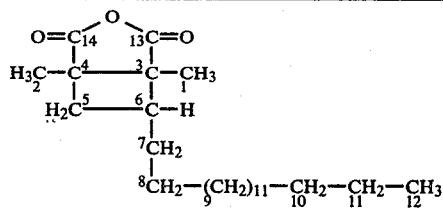

| C atom | $^{13}C$ δ tms |
|---|---|
| 1 | 9.6 |
| 2 | 17.3 |
| 3 | 50.8 |
| 4 | 46.7 |
| 5 | 37.0 |
| 6 | 39.8 |
| *7 | 32.6 |
| *8 | 27.5 |
| 9 | 30.4 |
| 10 | 31.9 |
| 11 | 23.3 |
| 12 | 14.5 |
| *13 | 175.8 |
| *14 | 176.5 |

*assignments could be reversed.

EXAMPLE 3

A mixture of 7.56 g (60 mm) of dimethylmaleic anhydride, 13.35 ml (60 mm) of 1-dodecene, 0.5 g of benzophenone, and 50 ml of isopropyl ether was refluxed over a G. E. Sunlamp for 24 hours. The mixture was cooled to 20° C., filtered from 0.7 g of dimethylmaleic anhydride photo-dimer, and evaporated. The solid was dried on clay plate, giving 15.4 g (87.3%) of white solid m p 44°–46° C., that analyzed C,73.1%; H,9.8% Calcd. for $C_{18}H_{30}O_3$: C,73.5%; H,10.2%.

EXAMPLE 4

A mixture of 4.1 ml (30 mm) of dicyclopentadiene, 0.5 g of benzophenone, 7.56 g (60 mm) of dimethylmaleic anhydride, and 50 ml of isopropyl ether was refluxed over a G. E. Sunlamp for 17 hours. The mixture was evaporated, the residue extracted with cold acetone, in which the photo-dimer of dimethylmaleic anhydride is insoluble, and the acetone extract evaporated, giving 4.25 g. (55%) of a white solid melting at 168°–175° C. Analysis: Calcd. for $C_{16}H_{18}O_3$: C,74.4%; H,7.0%. Found: C,73.8%; H,7.0%. The product probably is a mixture of:

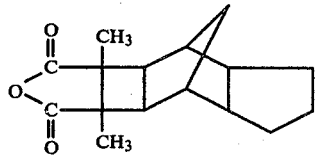

and

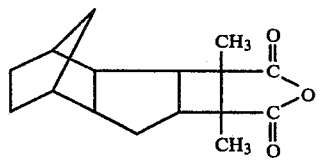

The products of Examples 1, 2, and 3 were tested as rust inhibitors by the method of N.A.C.E. (National Association of Corrosion Engineers) TM-01-72, a modification of ASTM D-665. The products, each in 300 ml of test fuel, an unleaded gasoline, at the concentration of 1 lb./1000 barrels, 3.8 ppm, were kept at 100° F., a polished steel test bar added, and the fuel solution stirred 30 minutes at 100° F. Distilled water, 30 ml. was added and stirring was continued for 3.5 hours. The steel test bars were withdrawn and rated by estimating the area covered with rust, using this scale:

| A | no rust |
|---|---|
| B++ | 0.1% rust |
| B+ | 5% rust |
| B | 5–25% rust |
| C | 25–50% rust |
| D | 50–75% rust |
| E | 75–100% rust |

| Compound of Example | Rating |
|---|---|
| — (blank, no additive) | E |
| 1 | B |
| 2 | B+ |
| 3 | B |
| H-3687 (dimerized linoleic acid) | B+ |

The compounds of our invention may be used in fuels and lubricants at 1 to 10,000 parts per million.

We claim:

1. Photo-adducts of dimethyl maleic anhydride and olefins as rust inhibitors in concentrations of about 0.0001 to 1 weight percent in fuels and oils.

2. The rust inhibitor of claim 1 wherein it is a mixture of:

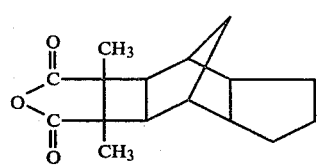

and

-continued
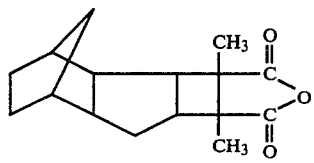
3. The rust inhibitor of claim 1 wherein it is of the following composition:
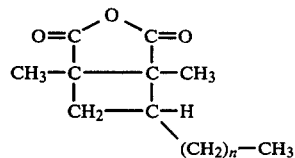
wherein n is 5 through 27.
* * * * *